(12) United States Patent
Harris

(10) Patent No.: US 6,689,169 B2
(45) Date of Patent: Feb. 10, 2004

(54) PROTHESIS

(75) Inventor: David Harris, Shrewsbury (GB)

(73) Assignee: Finsbury (Development) Limited, Leatherhead (GB)

( * ) Notice: Subject to any disclaimer, the term of this patent is extended or adjusted under 35 U.S.C. 154(b) by 0 days.

(21) Appl. No.: 10/003,647

(22) Filed: Nov. 2, 2001

(65) Prior Publication Data

US 2002/0055785 A1 May 9, 2002

(30) Foreign Application Priority Data

Nov. 3, 2000 (EP) ............................................. 00309759

(51) Int. Cl.$^7$ .................................................. A61F 2/42
(52) U.S. Cl. .................................................. 623/21.16
(58) Field of Search ........................... 623/21.11, 21.15, 623/21.16, 21.17, 22.39, 23.4

(56) References Cited

U.S. PATENT DOCUMENTS

| | | | |
|---|---|---|---|
| 3,875,594 A | | 4/1975 | Swason |
| 3,946,445 A | | 3/1976 | Bentley et al. |
| 4,304,011 A | * | 12/1981 | Whelan, III |
| 4,352,212 A | * | 10/1982 | Greene et al. |
| 4,725,280 A | | 2/1988 | Laure |
| 5,007,932 A | | 4/1991 | Bekki et al. |
| 5,147,386 A | * | 9/1992 | Carignan et al. |

FOREIGN PATENT DOCUMENTS

| | | | |
|---|---|---|---|
| DE | 19628476 | * | 1/1997 |
| EP | 0 338 715 | | 10/1989 |
| EP | 0 611 560 | | 8/1994 |
| FR | 2 605 878 | | 5/1988 |
| FR | 2 717 071 | | 9/1995 |
| FR | 2 734 150 | | 11/1996 |
| FR | 2 742 043 | | 6/1997 |
| GB | 2 045 085 | | 10/1980 |
| GB | 2 308 068 | | 6/1997 |
| WO | WO 81/00511 | | 3/1981 |
| WO | WO 91/04718 | | 4/1991 |
| WO | WO 95/09587 | | 4/1995 |
| WO | WO 95/09588 | | 4/1995 |
| WO | WO 95/33425 | * | 12/1995 |
| WO | WO 98/57600 | | 12/1998 |

OTHER PUBLICATIONS

N. Berme, J. P. Paul and W. K. Purves, A Biomechanical Analysis of the Metacarpophalangeal Joint, 1977, pp. 409–412, vol. 10, Pergamon Press, Great Britain.

Arthor D. Steffee, MD, Robert D. Beckenbaugh, MD, Ronald L. Linscheid, MD and James H. Dobyns, MD, The Development, Technique, and Early Clinical Results of Total Joint Replacement for the Metacarpophalangeal Joint of the Fingers, Total Metacarpophalangeal Arthroplasty, Feb. 1981, pp. 175–180, Vol 4/No 2.

European Search Report, 2 pages, Jun. 7, 2001 EP 00 309759.

* cited by examiner

Primary Examiner—Ralph A. Lewis

(57) ABSTRACT

A prosthesis for a metacarpophalangeal joint comprises a metacarpal plug member, a metacarpal insert member, and a phalangeal insert member. The metacarpal plug member comprises an elongate body which generally tapers from a proximal end to a distal end, an axial bore, and a plurality of axially spaced first fins projecting from the elongate body. The metacarpal insert member comprising a head portion having a convex articulating surface and a stem portion. The phalangeal insert member comprises an enlarged proximal end portion and an elongate shaft portion. The enlarged end portion is provided with a concave articulating surface substantially congruent with the convex articulating surface of the metacarpal insert member, and the elongate shaft portion tapers generally towards a distal end of the phalangeal insert member, and is provided with a plurality of axially spaced second fins projecting therefrom.

23 Claims, 2 Drawing Sheets

PROTHESIS

BACKGROUND OF THE INVENTION

This invention relates to a prosthesis, particularly a prosthesis suitable for replacement of a metacarpophalangeal joint, i.e a knuckle joint.

Damage may be sustained by the joints in the hand due to various reasons, but the most common are osteoarthritis and rheumatoid arthritis. Osteoarthritis occurs as a result of injury to the hands and is specific to an affected area, i.e. where the damage occurred. The finger joints have no protection, unlike the knee joint which is protected by the knee cap, and therefore the articular surfaces may be easily damaged through injury.

Rheumatoid arthritis is a progressive, debilitating disease which attacks many joints in the body. A typical indication of rheumatoid arthritis is the occurrence of ulnar drift, where the metacarpophalangeal joint suffers particularly badly. This occurs because rheumatoid arthritis also significantly affects the soft tissue and tendons in the body which compounds the effects of the disease on the knuckle joints.

Some different aspects of hand function are described in an article "A biomechanical analysis of the metacarpophalangeal joint" by N. Berme et al, J. Biomechanics, 1977, Vol. 10, pages 409 to 412.

Various prostheses have been proposed in the past for replacement of the metacarpophalangeal joint. Early prostheses incorporated a constrained steel-hinge mechanism. Later designs utilise separate metacarpal and phalangeal components. For example, U.S. Pat. No. 3,946,445 describes a prosthesis comprising two components each having a rounded bearing body and an integrally projecting intramedullary stem. Ribs and grooves on the two components intermesh for component engagement and the metacarpal component body overhangs the stem at a concave rib end in order to provide knuckle simulation.

U.S. Pat. No. 5,007,932 describes an artificial bone joint suitable for replacing a knuckle joint having anchor portions fitted into the bone comprising recesses or bosses. These recesses or bosses face the direction of insertion of the anchor portion and form an angle of less than 100 degrees. This is said to overcome the long period of time that was previously required to allow embedding of the joint structure in the patient's articulation.

International Patent Publication No. WO 95/09587 describes a joint prosthesis which allows rotary circumduction and, therefore, is said to be particularly adapted for replacement of the thumb joint. The two components comprise saddle shaped articulating surfaces which bear upon each other in such a way as to allow the bones to move in rotary circumduction with respect to each other.

International Patent Publication No. WO 95/09588 describes a prosthesis for the replacement of joints between long bones in the hand, including metacarpophalangeal joints, comprising two components each having an elongate stem for reception in one of the elongate bones and each having lateral articulating surfaces. The lateral articulating surfaces engage and articulate with each other such that lateral articulation is restrained only when the bones are articulated through at least 30 degrees of flexion. Parts of the metacarpal and phalangeal bones must be removed in order to fit the prosthesis which is not fixed by bone cement. No provision is made in this design of prosthesis to prevent ulnar drift.

Historically interposition arthroplasty has proven to be haphazard. It is rare that full flexion and extension is achieved once a metacarpophalangeal prosthesis is fitted and bone erosion, even breakage, is a significant problem. When the prosthesis is not fixed into the bone it may flex and piston in and out of the bone which presents the opportunity for significant wear. Moreover loosening of prostheses used in the fingers is a problem in the same way as in other total joint replacements such as hip, knee and shoulder replacements. It has been postulated that the problem lies with the means of fixation of the prosthesis and that the subsidence which is seen in the hip joint is also a problem with metacarpophalangeal and proximal interphalangeal joints. Often the prosthesis migrates down the intramedullary canal.

In an article entitled "The development, technique, and early clinical results of total joint replacement for the metacarpophalangeal joint of the fingers", by Arthur D. Steffee et al., Orthopedics, February 1981, Vol 4/No. 2, pages 175 to 180, there is described a prosthesis which was developed with the aim of overcoming recurrent problems of ulnar drift and extensor lag. It is suggested that the addition of "wings" laterally on the plastic socket part of the prosthesis may help with alignment of the prosthesis in the canal, amongst other things.

A one piece prosthesis has been marketed under the name Silastic® HP 100 Swanson Finger Joint Implant. This is further described, for example, in U.S. Pat. No. 3,875,594.

In many cases the surgeon will decide to replace all of the metacarpophalangeal joints of a patient's hand. In order that the surgical procedure shall not be too extended, it is recognised that the time to replace each individual joint should desirably be as short as possible. Moreover the joint should mimic as nearly as possible the action of the natural joint.

SUMMARY OF THE INVENTION

There is a need in the art for an improved prosthesis for replacement of the metacarpophalangeal joint. In particular there is a need for a metacarpophalangeal joint prosthesis which can be surgically inserted in a short space of time. In addition there is a need for a prosthesis for a metacarpophalangeal joint which can be inserted without use of bone cement.

It is accordingly an object of the current invention to provide an improved prosthesis for metacarpophalangeal joint replacement. A further object is to provide a prosthesis for replacement of the metacarpophalangeal joint which prevents wear and potential breakage of bone while providing full flexion and extension of the joint.

According to the present invention there is provided a prosthesis for a metacarpophalangeal joint comprising:

a metacarpal plug member for reception in a surgically prepared bore in a metacarpal bone comprising an elongate body which generally tapers from a proximal end to a distal end, which has a central longitudinal axis extending from the proximal end to the distal end, and which is formed with an axial bore extending from the proximal end towards the distal end, and a plurality of axially spaced first fins projecting from the elongate body in a direction substantially perpendicular to the central longitudinal axis of the elongate body for locating the metacarpal plug member in the surgically prepared bore in the metacarpal bone;

a metacarpal insert member comprising a head portion having a convex articulating surface and a stem portion projecting distally from the head portion for reception in the proximal end of the axial bore of the metacarpal plug member; and a phalangeal insert member for reception in a surgically prepared bore in a proximal phalangeal bone comprising an enlarged proximal end portion and an elongate shaft portion that extends distally from the enlarged proximal end portion, the enlarged end portion being provided with a concave articulating surface substantially congruent with the convex articulating surface of the metacarpal insert member, and the elongate shaft portion having a longitudinal axis, tapering generally towards a distal end of the phalangeal insert member, and being provided with a plurality of axially spaced second fins projecting therefrom in a direction substantially perpendicular to the longitudinal axis thereof for locating the phalangeal insert member in the surgically prepared bore in the proximal phalangeal bone.

Preferably the metacarpal plug member is formed from a biocompatible plastics material. Also the phalangeal insert member is preferably formed from a biocompatible plastics material. A suitable biocompatible plastics material is ultra high molecular weight polyethylene.

The metacarpal insert member is preferably formed from a biocompatible metal material. Suitable biocompatible metal materials include cobalt-chrome, titanium, titanium alloys, titanium coated cobalt-chrome, and stainless steel.

The first fins may be circular in shape but are preferably non-circular in shape. Hence in a preferred design of prosthesis according to the invention the first fins are substantially triangular in shape. They may have the corners of the triangular shape somewhat cropped so that the first fins have the shape of an irregular pentagon. In one design the metacarpal plug member is provided with four first fins. Typically the first fins are about 0.6 mm thick.

Suitably the diameter of the axial bore in the metacarpal plug member is about 3.0 mm.

The metacarpal plug member may have a dorsal chamfered face adjacent its proximal end which is adapted to mate with a corresponding surface on the distal side of the head portion of the metacarpal insert. In this case the dorsal chamfered face makes an angle of about 35° with the central longitudinal axis of the metacarpal plug member.

The convex articulating surface of the metacarpal insert member preferably defines part of a substantially spherical surface whose radius of curvature preferably ranges from 4.75 mm to 8.5 mm, corresponding to nominal sizes of from 9.5 mm to 17 mm. In the 17 mm nominal size the radius of curvature of the substantially spherical surface is 8.5 mm, while this radius is 4.75 mm for a nominal size of 9.5 mm, 6 mm for a nominal size of 12 mm, and 7.25 mm for a nominal size of 14.4 mm.

Desirably the head portion of the metacarpal insert member is formed with a dorsal groove for receipt of an extensor tendon.

The stem portion of the metacarpal insert member may have a polished surface. In this case the stem portion can be free to move within the axial bore in the metacarpal plug member.

Alternatively the stem portion of the metacarpal insert may have a roughened surface. In this case movement of the stem portion can be restricted once received within the axial bore in the metacarpal plug member.

Yet again the stem portion can be a clip-fit within the axial bore in the metacarpal plug member.

Preferably the second fins are substantially oval in shape and may be about 0.6 mm thick.

In one preferred design the concave articulating surface is positioned asymmetrically with respect to the longitudinal axis of the phalangeal insert member so as to cause the center of rotation of the prosthesis to drop from the longitudinal axis of the phalangeal insert member.

BRIEF DESCRIPTION OF THE DRAWINGS

In order that the invention may be clearly understood and readily carried into effect an embodiment thereof will now be described, by way of example only, with reference to the accompanying drawings, wherein.

DETAILED DESCRIPTION OF THE PREFERRED EMBODIMENTS

Figure 1:
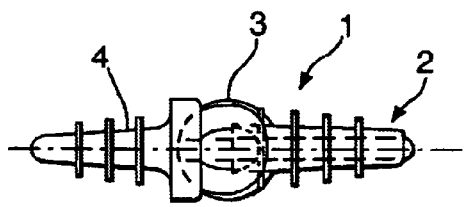
FIG. 1 is a top plan view of a metacarpophalangeal prosthesis in accordance with the invention.

Referring to the drawings, and particularly to FIG. 1 thereof, a metacarpophalangeal prosthesis 1 of nominal size 17 mm and constructed in accordance with the invention comprises a metacarpal plug 2, which is made of a resilient biocompatible plastics material such as ultra high molecular weight polyethylene, a metacarpal insert 3 made of a biocompatible metal or alloy, such as cobalt-chrome (i.e. a cobalt/chromium alloy), titanium, or titanium coated cobalt-chrome, and a phalangeal insert 4 made of a biocompatible plastics material, such as ultra high molecular weight polyethylene.

Figure 2:
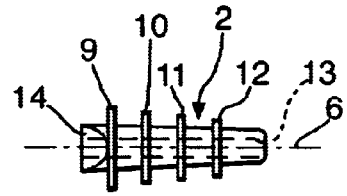
FIG. 2 is a top plan view of a metacarpal plug forming part of the prosthesis of FIG. 1.
Figure 3:
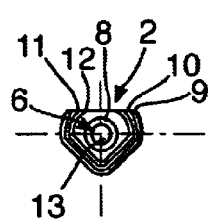
FIG. 3 is an end view of the plug of FIG. 2.
Figure 4:
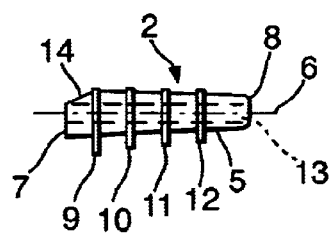
FIG. 4 is a side view of the plug of FIGS. 2 and 3.

FIGS. 2 to 4 illustrate the metacarpal plug 2 in greater detail. This consists of a hollow plug for insertion into a suitably prepared proximal phalangeal bone of the hand which comprises an elongate body 5 having a central longitudinal axis 6. Body 5 tapers from a proximal end 7 to a distal end 8 and has a plurality of axially spaced fins 9, 10, 11 and 12 which project from the elongate body 5 in a direction generally perpendicular to central longitudinal axis 6.

As can be seen from FIG. 3, which is an end view from the distal end 8 of plug 2, the elongate body 5 is substantially triangular in section with the corners cut off to form an irregular pentagon. A bore 13 which is typically 3.0 mm in diameter extends through plug 2 for a purpose which will be explained below.

Adjacent its proximal end 7 plug 2 has a dorsal chamfered surface 14 which makes an angle of about 35° to longitudinal axis 6.

Figure 5:
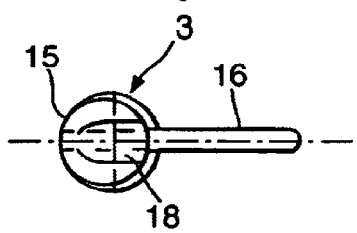
FIG. 5 is a top plan view of a metacarpal insert forming part of the metacarpophalangeal prosthesis of FIG. 1 adapted for insertion in the plug of FIGS. 2 to 4.
Figure 6:
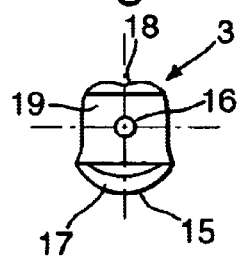
FIG. 6 is an end view of the metacarpal insert of FIG. 5.
Figure 7:
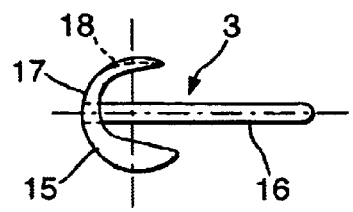
FIG. 7 is a side view of the metacarpal insert of FIGS. 5 and 6.

FIGS. 5 to 7 illustrate the metacarpal insert 3. As can be seen from FIG. 5, metacarpal insert 3 comprises a head portion 15 and a stem 16 projecting distally from the head portion 15 for reception in the bore 13. The diameter of stem 16 is typically 3.0 mm, i.e. the same as the diameter of bore 13. This ensures a tight fit between the stem 16 of metacarpal insert 3 and the metacarpal plug 2 when the stem 16 is received therein. The head portion 15 has a convex articulating surface 17 which defines a substantially single radius surface with a radius of curvature of 8.5 mm.

FIG. 6 is an end view of metacarpal insert 3 from the distal end of stem 16. In this Figure there can be seen a rounded groove 18 on the dorsal side of surface 17 to accommodate the extensor tendon. The distal surface 19 of metacarpal insert 3 is shaped to mate with the chamfered surface 14 on the metacarpal plug 2.

Figure 8:
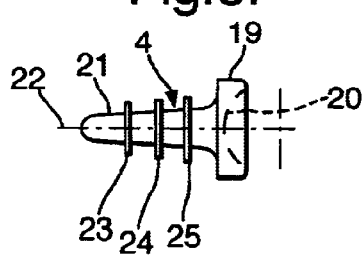
FIG. 8 is a top plan view of a phalangeal insert forming part of the prosthesis of FIG. 1.
Figure 9:
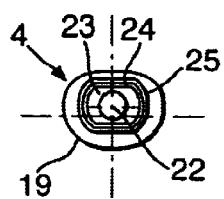
FIG. 9 is and end view of the phalangeal insert of FIG. 8.
Figure 10:
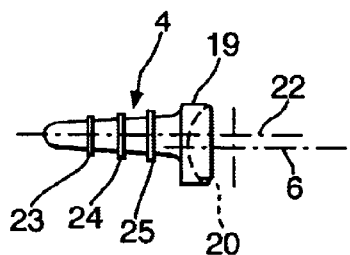
FIG. 10 is a side view of the phalangeal insert of FIGS. 8 and 9.

Referring now to FIGS. 8 to 10 of the drawings, the phalangeal insert 4 for reception in the proximal phalangeal bone of the hand comprises an enlarged end portion 19 having a single radius concave articulating surface 20 whose radius of curvature is 8.5 mm. Hence the concave articulating surface 20 is substantially congruent with the convex articulating surface 15 of the metacarpal insert 3. Extending distally from enlarged proximal end portion 19 is a shaft portion 21 with a longitudinal axis 22. A plurality of axially spaced second fins 23, 24 and 25 which are substantially oval in shape project from the shaft portion 21 in a direction generally perpendicular to the longitudinal axis 22. As can be seen from FIGS. 8 to 10, shaft portion 21 generally tapers from the proximal end to the distal end of phalangeal insert 4.

As is apparent from inspection of FIG. 10, the concave articulating surface 20 is positioned asymmetrically with respect to the longitudinal axis 22. In this way the center of rotation of the prosthesis is dropped somewhat from the longitudinal axis of the phalangeal insert 4. This is indicated in FIG. 10 which also depicts the position of central longitudinal axis 6 of the metacarpal plug member 2 as if the finger is fully extended.

Although the illustrated metacarpophalangeal joint has been described as having a polished stem 16 so as to permit it to slide axially in the bore 13, it could alternatively be provided with a roughened surface so as to hinder it sliding in the bore 13. Another possibility is to form it so that it engages in the bore 13 with a push-fit action thereby effectively locking the stem 16 against sliding in the bore 13.

Figure 11:
FIGS. 11 to 13 are top plan views of other sizes of metacarpophalangeal prostheses in accordance with the invention.
Figure 12:
Figure 13:

Since the sizes of the knuckle joint can vary from one finger to another of a patient's hand and from one patient to another, it will normally be preferred for the manufacturer of prostheses in accordance with the invention to provide a range of different sizes suitable for fitting different sizes of metacarpophalangeal joint. A typical range of sizes would include nominal sizes of 9.5 mm, 12 mm, 14.5 mm and 17 mm respectively. In the 17 mm nominal size the radius of curvature of the substantially spherical surface is 8.5 mm, while this radius is 4.75 mm for a nominal size of 9.5 mm, 6 mm for a nominal size of 12 mm, and 7.25 mm for a nominal size of 14.4 mm. FIGS. 11 to 13 are top plan views, similar to that of FIG. 1, of a 9.5 mm nominal size metacarpophalangeal prosthesis, of a 12 mm nominal size metacarpophalangeal prosthesis, and of a 14.5 mm nominal size prosthesis respectively.

What is claimed is:

1. A prosthesis for a metacarpophalangeal joint comprising:
   a metacarpal plug member formed from a resilient biocompatible plastics material for reception in a surgically prepared bore in a metacarpal bone comprising an elongate body having a tapered external surface which generally tapers from a proximal end to a distal end, which has a central longitudinal axis extending from the proximal end to the distal end, and which is formed with an axial bore extending from the proximal end towards the distal end, and a plurality of axially spaced first fins projecting from the tapered external surface of the elongate body in a direction substantially perpendicular to the central longitudinal axis of the elongate body for locating the elongate body of the metacarpal plug member in the surgically prepared bore in the metacarpal bone, the fins having free ends spaced radially outward from the tapered external surface of the elongate body for contact with the walls of the surgically prepared bore in the metacarpal bone so that the elongate tapered body of the metacarpal plug member is spaced in from the walls of the surgically prepared bore in the metacarpal bone;
   a metacarpal insert member formed from a biocompatible metal material comprising a head portion having a convex articulating surface and a stem portion projecting distally from the head portion for reception in the proximal end of the axial bore of the metacarpal plug member; and
   a phalangeal insert member formed from a resilient biocompatible plastics material for reception in a surgically prepared bore in a proximal phalangeal bone comprising an enlarged proximal end portion and an elongate shaft portion that extends distally from the enlarged proximal end portion, the enlarged end portion being provided with a concave articulating surface substantially congruent which the convex articulating surface of the metacarpal insert member, and the elongate shaft portion having a longitudinal axis and a tapered external surface, tapering generally towards a distal end of the phalangeal insert member, and being provided with a plurality of axially spaced second fins which are substantially oval in shape projecting from the tapered external surface in a direction substantially perpendicular to the longitudinal axis thereof for locating the elongate shaft portion of the phalangeal insert member in the surgically prepared bore in the proximal phalangeal bone, the fins having free ends spaced radially outward from the tapered external surface of the elongate shaft portion for contact with the walls of the surgically prepared bore in the proximal phalangeal bone so that the elongate tapered shaft portion of the phalangeal insert member is spaced in from the walls of the surgically prepared bore in the proximal phalangeal bone.

2. A prosthesis according to claim 1, wherein the biocompatible plastics material is high molecular weight polyethylene.

3. A prosthesis according to claim 1, wherein the metacarpal insert member is formed from a biocompatible metal material.

4. A prosthesis according to claim 1, wherein the biocompatible metal material is selected from cobalt-chrome, titanium, titanium alloys, titanium coated cobalt-chrome, and stainless steel.

5. A prosthesis for a metacarpophalangeal joint comprising:
   a metacarpal plug member for reception in a surgically prepared bore in a metacarpal bone comprising an elongate body which generally tapers from a proximal end to a distal end, which has a central longitudinal axis extending from the proximal end to the distal end, and which is formed with an axial bore extending from the proximal end towards the distal end, and a plurality of axially spaced first fins which are substantially triangular in shape projecting from the elongate body in a direction substantially perpendicular to the central longitudinal axis of the elongate body for locating the metacarpal plug member in the surgically prepared bore in the metacarpal bone;

a metacarpal insert member comprising a head portion having a convex articulating surface and a stem portion projecting distally from the head portion for reception in the proximal end of the axial bore of the metacarpal plug member; and a phalangeal insert member for reception in a surgically prepared bore in a proximal phalangeal bone comprising an enlarged proximal end portion and an elongate shaft portion that extends distally from the enlarged proximal end portion, the enlarged end portion being provided with a concave articulating surface substantially congruent with the convex articulating surface of the metacarpal insert member, and the elongate shaft portion having a longitudinal axis, tapering generally towards a distal end of the phalangeal insert member, and being provided with a plurality of axially spaced second fins projecting therefrom in a direction substantially perpendicular to the longitudinal axis thereof for locating the phalangeal insert member in the surgically prepared bore in the proximal phalangeal bone.

6. A prosthesis according to claim 5, wherein the metacarpal plug member is provided with four first fins.

7. A prosthesis according to claim 5, wherein the first fins are about 0.6 mm thick.

8. A prosthesis according to claim 5, wherein the diameter of the axial bore in the metacarpal plug member is about 3.0 mm.

9. A prosthesis according to claim 5, wherein the convex articulating surface of the metacarpal insert member defines part of a substantially spherical surface.

10. A prosthesis according to claim 9, wherein the radius of curvature of the substantially spherical surface ranges from about 8 mm to about 18 mm.

11. A prosthesis according to claim 9, wherein the radius of curvature of the substantially spherical surface is 4.75 mm, 6 mm, 7.25 mm or 8.5 mm.

12. A prosthesis according to claim 5, wherein the head portion of the metacarpal insert member is formed with a dorsal groove for receipt of an extensor tendon.

13. A prosthesis according to claim 5, wherein the stem portion of the metacarpal insert member has a polished surface.

14. A prosthesis according to claim 13, wherein the stem portion is free to move within the axial bore in the metacarpal plug member.

15. A prosthesis according to claim 5, wherein the stem portion of the metacarpal insert has a roughened surface.

16. A prosthesis according to claim 15, wherein movement of the stem portion is restricted once received within the axial bore in the metacarpal plug member.

17. A prosthesis according to claim 5, wherein the second fins are about 0.6 mm thick.

18. A prosthesis according to claim 5, wherein there are three second fins.

19. A prosthesis according to claim 5, wherein the concave articulating surface is positioned asymmetrically with respect to the longitudinal axis of the phalangeal insert member so as to cause the centre of rotation of the prosthesis to drop from the longitudinal axis of the phalangeal insert member.

20. A prosthesis for a metacarpophalangeal joint comprising:

a metacarpal plug member for reception in a surgically prepared bore in a metacarpal bone comprising an elongate body which generally tapers from a proximal end to a distal end, which has a central longitudinal axis extending from the proximal end to the distal end, and which is formed with an axial bore extending from the proximal end towards the distal end, and a plurality of axially spaced first fins which have the shape of an irregular pentagon projecting from the elongate body in a direction substantially perpendicular to the central longitudinal axis of the elongate body for locating the metacarpal plug member in the surgically prepared bore in the metacarpal bone;

a metacarpal insert member comprising a head portion having a convex articulating surface and a stem portion projecting distally from the head portion for reception in the proximal end of the axial bore of the metacarpal plug member; and a phalangeal insert member for reception in a surgically prepared bore in a proximal phalangeal bone comprising an enlarged proximal end portion and an elongate shaft portion that extends distally from the enlarged proximal end portion, the enlarged end portion being provided with a concave articulating surface substantially congruent with the convex articulating surface of the metacarpal insert member, and the elongate shaft portion having a longitudinal axis, tapering generally towards a distal end of the phalangeal insert member, and being provided with a plurality of axially spaced second fins projecting therefrom in a direction substantially perpendicular to the longitudinal axis thereof for locating the phalangeal insert member in the surgically prepared bore in the proximal phalangeal bone.

21. A prosthesis for a metacarpophalangeal joint comprising:

a metacarpal plug member for reception in a surgically prepared bore in a metacarpal bone comprising an elongate body which generally tapers from a proximal end to a distal end, which has a central longitudinal axis extending from the proximal end to the distal end, and which is formed with an axial bore extending from the proximal end towards the distal end, and a plurality of axially spaced first fins projecting from the elongate body in a direction substantially perpendicular to the central longitudinal axis of the elongate body for locating the metacarpal plug member in the surgically prepared bore in the metacarpal bone;

a metacarpal insert member comprising a head portion having a convex articulating surface and a stem portion projecting distally from the head portion for reception in the proximal end of the axial bore of the metacarpal plug member; and a phalangeal insert member for reception in a surgically prepared bore in a proximal phalangeal bone comprising an enlarged proximal end portion and an elongate shaft portion that extends distally from the enlarged proximal end portion, the enlarged end portion being provided with a concave articulating surface substantially congruent with the convex articulating surface of the metacarpal insert member, and the elongate shaft portion having a longitudinal axis, tapering generally towards a distal end of the phalangeal insert member, and being provided with a plurality of axially spaced second fins projecting therefrom in a direction substantially perpendicular to the longitudinal axis thereof for locating the phalangeal insert member in the surgically prepared bore in the proximal phalangeal bone;

said metacarpal plug member having a dorsal chamfered face adjacent its proximal end which is adapted to mate with a corresponding surface on the distal side of the head of the metacarpal insert.

22. A prosthesis for a metacarpophalangeal joint comprising:

a metacarpal plug member for reception in a surgically prepared bore in a metacarpal bone comprising an elongate body which generally tapers from a proximal end to a distal end, which has a central longitudinal axis extending from the proximal end to the distal end, and which is formed with an axial bore extending from the proximal end towards the distal end, and a plurality of axially spaced first fins projecting from the elongate body in a direction substantially perpendicular to the central longitudinal axis of the elongate body for locating the metacarpal plug member in the surgically prepared bore in the metacarpal bone;

a metacarpal insert member comprising a head portion having a convex articulating surface and a stem portion projecting distally from the head portion for reception in the proximal end of the axial bore of the metacarpal plug member; and a phalangeal insert member for reception in a surgically prepared bore in a proximal phalangeal bone comprising an enlarged proximal end portion and an elongate shaft portion that extends distally from the enlarged proximal end portion, the enlarged end portion being provided with a concave articulating surface substantially congruent with the convex articulating surface of the metacarpal insert member, and the elongate shaft portion having a longitudinal axis, tapering generally towards a distal end of the phalangeal insert member, and being provided with a plurality of axially spaced second fins projecting therefrom in a direction substantially perpendicular to the longitudinal axis thereof for locating the phalangeal insert member in the surgically prepared bore in the proximal phalangeal bone;

said metacarpal plug member having a dorsal chamfered face adjacent its proximal end which is adapted to mate with a corresponding surface on the distal side of the head of the metacarpal insert; and said dorsal chamfered face making an angle of about 35° with the central longitudinal axis of the metacarpal plug member.

23. A prosthesis for a metacarpophalangeal joint comprising:

a metacarpal plug member for reception in a surgically prepared bore in a metacarpal bone comprising an elongate body which generally tapers from a proximal end to a distal end, which has a central longitudinal axis extending from the proximal end to the distal end, and which is formed with an axial bore extending from the proximal end towards the distal end, and a plurality of axially spaced first fins projecting from the elongate body in a direction substantially perpendicular to the central longitudinal axis of the elongate body for locating the metacarpal plug member in the surgically prepared bore in the metacarpal bone;

a metacarpal insert member comprising a head portion having a convex articulating surface and a stem portion projecting distally from the head portion for reception in the proximal end of the axial bore of the metacarpal plug member, the stem portion being a clip-fit within the axial bore in the metacarpal plug member; and a phalangeal insert member for reception in a surgically prepared bore in a proximal phalangeal bone comprising an enlarged proximal end portion and an elongate shaft portion that extends distally from the enlarged proximal end portion, the enlarged end portion being provided with a concave articulating surface substantially congruent with the convex articulating surface of the metacarpal insert member, and the elongate shaft portion having a longitudinal axis, tapering generally towards a distal end of the phalangeal insert member, and being provided with a plurality of axially spaced second fins projecting therefrom in a direction substantially perpendicular to the longitudinal axis thereof for locating the phalangeal insert member in the surgically prepared bore in the proximal phalangeal bone.

\* \* \* \* \*